US006187566B1

(12) United States Patent
Dattagupta et al.

(10) Patent No.: US 6,187,566 B1
(45) Date of Patent: Feb. 13, 2001

(54) METHOD OF LABELING A NUCLEIC ACID AMPLICON WITH SIMULTANEOUS CONTAMINATION PREVENTION

(75) Inventors: Nanibhushan Dattagupta; C. Nagaraja Sridhar; Whei-Kuo Wu, all of San Diego, CA (US)

(73) Assignee: Applied Gene Technologies, Inc., San Diego, CA (US)

( * ) Notice: Under 35 U.S.C. 154(b), the term of this patent shall be extended for 0 days.

(21) Appl. No.: 09/265,127

(22) Filed: Mar. 9, 1999

(51) Int. Cl.$^7$ ..................................................... C12P 19/34

(52) U.S. Cl. ................................ 435/91.1; 435/6; 435/4; 435/7; 435/18; 436/63; 436/94; 436/501; 436/504; 935/77; 935/78; 536/27

(58) Field of Search .................................... 435/6, 4, 91.1, 435/7, 18, 28, 188; 935/77, 78; 536/27; 436/63, 94, 501, 504; 546/109; 548/303

(56) References Cited

U.S. PATENT DOCUMENTS

| | | |
|---|---|---|
| 4,582,789 | 4/1986 | Sheldon, III et al. . |
| 4,683,195 | 7/1987 | Mullis et al. . |
| 4,683,202 | 7/1987 | Mullis et al. . |
| 4,734,454 | 3/1988 | Dattagupta et al. . |
| 5,026,840 | 6/1991 | Dattagupta et al. . |
| 5,221,608 | 6/1993 | Cimino et al. . |
| 5,348,855 | 9/1994 | Dattagupta et al. . |
| 5,409,818 | 4/1995 | Davey et al. . |
| 5,554,517 | 9/1996 | Davey et al. . |
| 5,792,614 | 8/1998 | Western et al. . |

OTHER PUBLICATIONS

Cimino, et al., "Post–PCR sterilization: a method to control carryover contamination for the polymerase chain reaction", *Nucleic Acid Res.*, 19(1):99–107 (1990).
Walder, et al., "Use of PCR primers containing a 3'–terminal ribose residue to prevent cross–contamination of amplified sequences", *Nucleic Acid Res.*, 21(18):4339–4343 (1993).
Chaires, et al., "Structure–Based Design of a New Bisintercalating Anthracycline Antibiotic", *J. Med. Chem.*, 40:261–266 (1977).
Chaires, et al., "Parsing the Free Energy of Anthracycline Antibiotic Binding to DNA", *Biochem.*, 35:2047–2053 (1996).
Haq, et al., "Specific Binding of Hoechst 33258 to the d(CGCAAATTTGCG)$_2$ Duplex: Calorimetric and Spectroscopic Studies", *J. Mol. Biol.*, 271:244–257 (1997).
Whelan, et al., "Direct Genotypic Detection of *Mycobacterium tuberculosis* Rifampin Resistance in Clinical Specimens by Using Single–Tube Heminested PCR", *J. Clin. Microbiol.*, 33(3):556–561 (1995).
Dattagupta, et al., "Perspectives in Antiinfective Therapy", Jackson, et al., (Ed.) Friedr. Vieweg & Sohn Verlagsgesellschaft mbH, Braunschweig, 241–247 (1989).

Wylie, et al., "Comparative Evaluation of Chlamydiazyme, PACE 2, and AMP–CT Assays for Detection of *Chlamydia trachomatis* in Endocervical Specimens", *J. Clin. Microbiol.*, 36(12):3488–3491 (1998).
Moore, et al., "Detection and Identification of *Mycobacterium tuberculosis* Directly from Sputum Sediments by Ligase Chain Reaction", *J. Clin. Microbiol.*, 36(4):1028–1031 (1998).
Walker, et al., "Strand displacement amplification—an isothermal, in vitro DNA amplification technique", *Nucleic Acids Res.*, 20(7):1691–1696 (1992).
Heim, et al., "Highly sensitive detection of gene expression of an intronless gene: amplification of mRNA, but not genomic DNA by nucleic acid sequence based amplification (NASBA)", *Nucleic Acids Res.*, 26(9):2250–2251 (1998).
Marmur, "A Procedure for the Isolation of Deoxyribonucleic Acid from Micro–organisms", *J. Mol. Biol.*, 3:208–218 (1961).
Troesch, et al., "Mycobacterium Species Identification and Rifampin Resistance Testing with High–Density DNA Probe Arrays", *J. Clin. Microbiol.*, 37(1):49–55 (1999).
Della–Latta, et al., "Comprehensive Evaluation of Performance, Laboratory Application, and Clinical Usefulness of Two Direct Amplification Technologies for the Detection of *Mycobacterium tuberculosis* Complex", *Am. J. Clin. Pathol.*, 110:301–310 (1998).
Neumaier, et al., "Fundamentals of quality assessment of molecular amplification methods in clinical diagnostics", *Clin. Chem.*, 44(1):12–26 (1998).
Gelmini, et al., "Quantitative polymerase chain reaction–based homogeneous assay with fluorogenic probes to measure c–erbB–2 oncogene amplification", *Clin. Chem.*, 43(5):752–758 (1997).
Nazarenko, et al., "A closed tube format for amplification and detection of DNA based on energy transfer", *Nucleic Acids Res.*, 25(12):2516–2521 (1997).
Hu, et al., "Analytic Performance and Contamination Control Methods of a Ligase Chain Reaction DNA Amplification Assay for Detection of *Chlamydia trachomatis* in Urogenital Specimens", *Diagn. Microbiol. Infect. Dis.*, 24:71–76 (1996).

(List continued on next page.)

*Primary Examiner*—W. Gary Jones
*Assistant Examiner*—Janell E. Taylor
(74) *Attorney, Agent, or Firm*—Morrison & Foester LLP

(57) ABSTRACT

This invention relates to methods of amplifying nucleic acids to minimize contamination by products of earlier amplification reactions. More particularly, it relates to methods of using nucleic acid labels that inhibit further amplification of the amplicon, and compositions that are useful to accomplish this task. In particular, the present invention relates to photoreactive complexes of a binding ligand, a binding enhancer and a label.

45 Claims, No Drawings

OTHER PUBLICATIONS

Vaneecchoutte, et al., "The possibilities and limitations of nucleic acid amplification technology in diagnostic microbiology", *J. Med. Microbiol*, 46:188–194 (1997).

Oehlenschlager, et al., "Detection of HIV–1 RNA by nucleic acid sequence–based amplification combined with fluorescence correlation spectroscopy", *Proc. Natl. Acad. Sci. (USA)*, 93:12811–12816 (1996).

Tevere, et al., "Detection of *Mycobacterium tuberculosis* by PCR Amplification with Pan–Mycobacterium Primers and Hybridization to an *M. tuberculosis*–Specific Probe", *J. Clin. Microbiol.*, 34(4):918–923 (1996).

Pao, et al., "Inhibition of in vitro enzymatic DNA amplification reaction by ultra–violet light irradiation", *Molec. and Cell. Probes*, 7:217–219 (1993).

Rys, et al., "Preventing False Positives: Quantitative Evaluation of Three Protocols for Inactivation of Polymerase Chain Reaction Amplification Products", *J. Clin. Microbiol.*, 31(9):2356–2360 (1993).

METHOD OF LABELING A NUCLEIC ACID AMPLICON WITH SIMULTANEOUS CONTAMINATION PREVENTION

FIELD OF THE INVENTION

This invention relates to methods of amplifying nucleic acids to minimize contamination by products of earlier amplification reactions. More particularly, it relates to methods of using nucleic acid labels that inhibit further amplification of the amplicon.

BACKGROUND OF THE INVENTION

Detecting specific gene sequences in clinical samples that are associated with disease states or biological conditions is frequently hindered by the low copy number of these gene sequences in the sample. The ability to replicate these gene sequences to improve sensitivity has revolutionized modern molecular genetics. There are currently many different methods for amplifying nucleic acids in samples to improve assay sensitivity, such as: polymerase chain reaction (PCR) (U.S. Pat. Nos. 4,683,195 and 4,683,202); ligase chain reaction (LCR); nucleic acid sequence-based amplification (NASBA) (U.S. Pat. Nos. 5,409,818 and 5,554,517); strand displacement amplification (SDA); and transcription-mediated amplification (TMA).

Many of these methods are capable of providing more than one billion copies of a single target nucleic acid in a very short time. Accordingly, one of the principle problems of using amplification technologies is that they are susceptible to contamination by exogenous nucleic acids. Although the latter can be controlled using careful laboratory techniques, the former source of contamination is hard to avoid in laboratories that repetitively amplify the same target sequences. In either case, this exogenous nucleic acid may be amplified along with the target nucleic acid in a clinical sample, which may lead to erroneous results.

Many different protocols have been developed in the past several years to prevent carryover contamination. Some of these protocols involve chemical, photochemical and/or enzymatic methods to inactivate the amplicons to prevent them from serving as templates in subsequent amplification reactions. When such methods are combined with appropriate laboratory techniques, the frequency of contamination-associated false-positive results is reduced. Since many of these types of decontamination protocols interfere with the amplification reaction, they must be carried out after amplification has been completed.

One of the more recently described methods for preventing contamination involves the use of UV irradiation to photochemically modify amplicon nucleotide bases. Such irradiation in the presence of certain isopsoralen derivatives forms cyclobutane adducts with pyrimidine bases, and the nucleic acids with these modified bases are no longer capable of serving as templates for subsequent PCR (G. D. Cimino et al., Nucleic Acid Research, 19(l):99–107 (1990)). However, this method has been described as only being useful when carried out after amplification has been completed, since these base reactions are non-specific and the reactants may interfere with the integrity of the target nucleic acid and other reaction components (R. Y. Walder et al., Nucleic Acids Research, 21(18):4339–4343 (1993)). Moreover, most of these currently used methods are adapted for use in PCR. Thus, it is not well established that such methods are equally as effective in other types of amplification reactions. Nor have decontamination protocols been specifically designed to be carried out during any stage of the amplification reaction.

Detection of the amplified nucleic acids involves the use of a labeling compound or compounds that can be measured and quantified. Many such labeling compounds are well known in the art. However, every additional step in the amplification reaction introduces additional reagent costs and assay time. Recently, methods have been develop that allow for simultaneous labeling and decontamination using reagents that are capable of serving both purposes.

Accordingly, there is a need to provide for improved decontamination reagents and protocols that are adapted for use before the amplification reaction has been completed, and that are suitable for simultaneous decontamination and labeling.

SUMMARY OF THE INVENTION

The present invention provides compositions that are useful for labeling and decontaminating a nucleic acid amplification reaction product, also referred to herein as an "amplicon". Such compositions comprise "LACs", which are covalent or noncovalent complexes of a binding ligand, a binding enhancer and a label. As described herein, the binding ligand is a chemical moiety that binds to the amplicon and that, when activated by light, forms at least one covalent bond therewith. Also as described herein, the binding enhancer is a chemical moiety that has a specific affinity for nucleic acids when compared to its affinity for the non-nucleic acid components of amplification reactions. As provided herein, the label is a detectable chemical moiety, such as a fluorophore, a chemiluminescent label or other chromophore.

In one aspect of the present invention, the binding ligand is either an intercalator compound, such as a furocoumarin or a phenanthridine, or a nonintercalator compound, such as a benzimide, a netropsin or a distamycin. When the binding ligand is an intercalator compound, in a preferred embodiment, it is an angelicin derivative.

In another aspect of the present invention, the binding enhancer is also either an intercalator compound or a non-intercalator compound, such as an oligo pyrrole, a phenyl indole, a nucleic acid or a protein.

In one embodiment, the LAC of the present invention is a complex of at least two intercalator moieties and a label.

Another aspect of the present invention is a method for labeling or decontaminating a nucleic acid amplification reaction product comprising the steps of preparing a nucleic acid amplification reaction mixture, contacting the mixture with the compositions just described, and exposing the mixture to light of an appropriate length of time and wavelength to cause the binding ligand to become covalently attached to the nucleic acid amplification reaction product.

Other aspects of the invention are described throughout the specification.

DETAILED DESCRIPTION OF THE INVENTION

The present invention relates to a method of amplifying a target analyte nucleic acid to produce multiple copies of the target, i.e. the nucleic acid reaction products of the amplification reaction which are also referred to as "amplicons", and contacting the amplicons with a photoreactive compound, or "light-activated compound" ("LAC") that serves the dual purpose of labeling and "deactivating" the amplicons. The present invention also relates to compositions comprising such LACs. By "deactivating", it is meant that the photo-activated amplicons can no longer be amplified. In particular, the LAC is added to the amplification reaction before, during or after the nucleic acid amplification reaction. After the amplification reaction is completed, the reaction mixture is exposed to light of an appropriate wavelength to cause the labeling compound to become covalently linked to the amplicon. Thereafter, the amplicon is incapable of serving as a template for polymerization and thus prevented from contaminating subsequent amplification reactions.

Definitions

The following definitions are provided to further describe various aspects of the preferred embodiments of the present invention.

The term "amplification" is used to refer to a method for exponentially duplicating a target analyte nucleic acid in a sample to improve assay sensitivity. As described herein, many different methods for amplifying nucleic acids are known in the art. It should be understood that the particular amplification method employed in the practice of the present invention can vary depending on the type of target analyte, the type of sample, the desired sensitivity, and the like. The selection and performance of such amplification methods are not within the scope of the present invention.

The term "binding ligand" is used to refer to a compound that has an affinity for nucleic acids, such that it forms a reversible complex with nucleic acids, and is capable of being activated upon the application of an appropriate wavelength of light to form a covalent bond with the nucleic acids.

The term "binding enhancer" is used to refer to a chemical moiety that has a specific affinity for nucleic acids.

The term "label" is used to refer to any chemical group or moiety having a detectable physical property or any compound capable of causing a chemical group or moiety to exhibit a detectable physical property, such as an enzyme that catalyzes conversion of a substrate into a detectable product. The term "label" also encompasses compounds that inhibit the expression of a particular physical property. The label may also be a compound that is a member of a binding pair, the other member of which bears a detectable physical property.

The term "nucleic acid(s)" is used to refer to deoxyribonucleic acid (DNA) and ribonucleic acid (RNA) in any form, including inter alia, single-stranded, duplex, triplex, linear and circular forms. It also includes polynucleotides, oligonucleotides, chimeras of nucleic acids and analogues thereof. The nucleic acids described herein can be composed of the well-known deoxyribonucleotides and ribonucleotides composed of the bases adenosine, cytosine, guanine, thymidine, and uridine, or may be composed of analogues or derivatives of these bases. Additionally, various other oligonucleotide derivatives with non-conventional phosphodiester backbones are also included herein, such as phosphotriester, polynucleopeptides, methylphosphonate, phosphorothioate, polynucleotides primiss and the like.

The term "target analyte" is used to refer to the particular nucleic acid that a sample is suspected of containing. Such analytes include nucleic acids in biological samples, research materials, environmental samples, bodily fluids, and may be unpurified or purified using known methods. For an example of types of target analytes, see U.S. Pat. No. 5,792,614.

LAC Structure and Function

The LACs that are useful in the practice of the present invention are designed to be compatible with any target amplification protocol, and can be added to the amplification reaction before, during or after the initiation of the amplification reaction. In particular, the LACs of the present invention are designed to have an enhanced affinity for nucleic acids so that they will efficiently bind to nucleic acid in the presence of other sample and amplification reaction constituents, such as proteins, lipids, enzymes, multivalent cations, etc. Such enhanced affinity permits a lower concentration of LAC to be necessary for efficient decontamination and labeling. Thus, a noninhibitory amount of LAC can be added to the amplification reaction mixture before amplification has taken place. Thereafter, the LAC can be exposed to light to effect simultaneous decontamination and labeling.

In a preferred embodiment, the LACs of the present invention are complexes comprising a binding ligand ("binding ligand"), a nucleic acid binding enhancer ("binding enhancer"), and a label. Such complexes can be either linear or branched. An example of a linear complex is given below:

BINDING LIGAND-BINDING ENHANCER-LABEL

In this example, the binding enhancer serves as the linker between the binding ligand and the label. Alternatively, an example of a branched complex is given below:

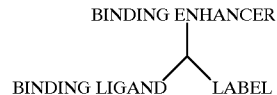

In this example, the binding ligand, binding enhancer and label are all interconnected to one another.

Binding Ligands

The binding ligand of the present invention is preferably any photoreactive chemical moiety that reversibly binds to nucleic acids and forms at least one covalent bond with the nucleic acid when exposed to light of an appropriate wavelength. In a preferred embodiment, the photoreactive binding ligand is an intercalator compound (i.e. a compound that interposes itself between the nucleotide bases of a nucleic acid helix). Suitable intercalator binding ligands include, inter alia, furocoumarins and phenanthridines. For binding to DNA, aminomethyl psoralen, aminomethyl angelicin and aminoalkyl ethidium or methidium azides are somewhat useful. Although these compounds preferentially bind to double-stranded DNA, conditions can be employed to denature the DNA to avoid simultaneous interaction of these compounds with two strands.

In order to preserve the ability of the labeled amplicon to participate in hybridization reactions, it is desirable to use binding ligands that react with a single nucleic acid strand. Accordingly, preferred binding ligands are "monoadduct" forming compounds such as isopsoralen or other angelicin derivatives, such as 4'-aminomethyl 0.4,5'-dimethyl angelicin, 4'-aminomethyl 4,5',8-trimethyl psoralen, 3-carboxy-5- or 8-amino- or hydroxy-psoralen, as well as mono- or bis-azido aminoalkyl methidium or ethidium compounds. For examples of other photoreactive intercalators, see U.S. Pat. No. 4,734,454. Nonintercalating compounds, such as diamidinoindophenol-bis-benzimidazoles, which are commonly known as Hoechst 33258 and 33342, and other benzimides, netropsins and distamycins can also be used in the present invention. Preferred photoreactive binding ligands are the monoadduct forming psoralens and isopsoralens.

Binding Enhancers

The LACs of the present invention also comprise a nucleic acid binding enhancer ("binding enhancer"), which serves to enhance the affinity of the LAC for nucleic acids above that exhibited with the binding ligand alone. Accordingly, binding enhancers tend to have a specific affinity for nucleic acids when compared to non-nucleic acid sample/reaction constituents. The binding enhancer may be the same as or different from the binding ligand. In other words, the binding ligand and the binding enhancer may each be an intercalator, wherein one of the two is a monoadduct-forming species, and the other is present to enhance binding by this monoadduct-forming species. Examples of such "dual role" binding ligands are described in J. B. Chaires, et al., *J. Med. Chem*, 40: 261–266 (1977). Therein, it has been described that binding of a bis-intercalating anthracycline antibiotic reached as high as $10^{11}$ at 20° C. It was also shown that the affinity of a similar monointercalator is not above $10^7$ (J. B. Chaire, et al., *Biochemistry*, 35: 2047–2053 (1996).

The binding enhancer can also be a non-intercalating compound. There are many nonintercalating nucleic acid binding molecules known in the art. A bis-benzimidazole derivative commonly known as Hoechst 33258 has shown affinity as high as $3.2 \times 10^8$ mole$^{-1}$. (Haq et al., *J. Mol. Biol.*, 271:244–257(1997).) Other non-intercalating binding enhancers are oligo pyrroles, phenyl indole derivatives and such molecules. These molecules do not bind nucleic acids only on the basis of positive charge. Other suitable binding enhancers bind nucleic acids on the basis of hydrogen bond formation, hydrophobic interaction in the groove and other nonionic interactions that give rise to high affinity reactions with nucleic acids. In general, preferred binding enhancers will exhibit an affinity for nucleic acids in an amount equal to or greater than $1 \times 10^4$ mole$^{-1}$. Other suitable binding enhancers include nucleic acids having a specific affinity for other nucleic acids, such as would be expected if the binding enhancer had a nucleic acid sequence complementary to that of the amplicon target nucleic acid. Yet other suitable binding enhancers include proteins that have a specific binding affinity for nucleic acids.

Not every compound capable of forming an electrostatic bond with a negatively charged nucleic acid can serve as a binding enhancer. For example, polycations such as polyamines are generally not suitable for use in the present invention because of their inability to specifically bind to nucleic acids in crude samples and in the presence of amplification reaction components. For example, such positively charged compounds will nonspecifically bind to all anionic macromolecules present in the sample, and not just to nucleic acids. In addition, the binding enhancer should be capable of specifically binding to nucleic acids in the presence of 10 to 20 mM magnesium, which is typically required for most amplification reactions. At this concentration, compounds that bind to nucleic acids solely on the basis of electrostatic interactions would not form stable complexes with nucleic acids and thus would require addition of a greater concentration of LAC for efficient labeling.

Labels

In the practice of the present invention, the binding ligand is either directly or indirectly linked to a label. Such attachment can be either covalent or ionic, so long as it is stable under the conditions in which the LAC is employed. Chemical attachments can be accomplished by any of a variety of well known methods. For example, if the binding ligand contains or is derivatised to contain an available carboxyl group and the label contains or is derivalized to contain an available amino group, the two can be reacted together to form an ester linkage. By "available", it is meant that the formation of a linkage will not interfere with the functioning of the label (i.e. its ability to be detected or to catalyze a detectable reaction) or the ligand (i.e. it's ability to bind nucleic acids.)

Particularly useful labels are enzymes, enzyme substrates, fluorophore, radiocsotopic compounds, chromophores, magnetically responsive compounds, antibody epitope-containing compounds, haptens, and the like.

Linkers

The binding ligand, binding enhancer, and label can also be indirectly attached via a linker. The linkers that are useful in the practice of the present invention are specifically designed to promote efficient binding of the binding ligand to the nucleic acids and functioning of the label attached thereto. They accomplish this by providing adequate physical separation between the two components of the LAC to prevent interference of one by the other. The use of linkers is described generally in U.S. Pat. Nos. 4,582,789 and 5,026,840. Certain compounds can serve the dual role of a binding enhancer and a linker. For example, linkers can be constructed from positively charged compounds, such that they enhance binding with negatively charged nucleic acids. However, in order for the linker to also serve as a binding enhancer, it is necessary for it to have a specific affinity for nucleic acids, and not just a non-structure specific electrostatic affinity for negatively charged compounds. Accordingly, the polyalkylamine linkers described in U.S. Pat. No. 5,026,840 are specifically excluded by the present invention as binding enhancers, although they may still be suitable for use as linkers.

In a preferred embodiment, a bifunctional linker is used that is capable of reacting with both the nucleic acid binding moiety and the label to form a chemical bridge therebetween. However, in an alternate embodiment, a multifunctional linker may be employed, to which the binding ligand, the binding enhancer and the label can all be attached to form a "branched" complex. Such complex formats and chemical reactions for forming these types of complexes are well known in the art.

Formulation and Use of LACs

The LACs of the present invention are useful for labeling and deactivating the amplicon products of nucleic acid amplification protocols. As such, they are generally prepared as an aqueous solution in an appropriate liquid medium at a concentration of around 10 micromolar to 10 millimolar. An aliquot of such solution is added to the amplification reaction mixture. The final preferable concentration of LAC in such a mixture is between about 1 micromolar and 1 millimolar, and more preferably the range is between about 0.01 micromolar and 0.1 millimolar. Depending on the LAC's affinity, concentrations lower than 0.01 micromolar would also function in instances where the affinity of the LAC for the nucleic acid was high. For deactivation and labeling, less than one LAC per twenty nucleotides is sufficient. Accordingly, efficiency of labeling can easily be achieved by using less than a ten to one ratio of LAC to nucleic acid. Determining the appropriate ratio would be a matter of routine optimization.

The aqueous medium for the LAC solution can be water or a buffer solution, the pH of which should preferably be such that the compound is stable. Such stability can be determined or easily assessed. For example, if a LAC with acridinium ester is used, the pH should not be alkaline. Otherwise, for most compounds, the pH can be between 3 and 12. Preferably, the pH is between 5 and 11 for compounds that have no acridinium ester or other alkali-hydrolysable moiety. Appropriate concentrations can also be determined by measuring the affinity of a specific LAC for nucleic acids and optimizing the binding conditions by methods known in the art. Such affinity values can be used to determine what concentration would produce a labeling efficiency of choice.

Another feature of the present invention is that the LAC, once light-activated, prevents the amplicon from being amplified in a subsequent amplification reaction. Accordingly, it is necessary to add sufficient LAC to the amplification reaction to essentially completely "deactivate" the labeled amplicons, without inhibiting subsequent detection reactions which may or may not depend on the amplicon's ability to hybridize. One of skill in the art could easily determine the least amount and greatest amount of LAC to be added to any given amplification reaction by carrying out simple optimization studies on a research scale.

The LACs of the present invention can be added to the amplification reaction before or after amplification has been carried out. It is generally not suitable for the LAC formulation to be added during the amplification reaction, since it is important to keep the reaction mixture closed to the environment to avoid contamination. However, if an appropriate reaction vessel is designed wherein the LAC can be added at some stage after amplification has begun but before it has been stopped without exposing the reaction mixture to the environment, one could easily envision that the LAC could be added during the amplification reaction. Since many amplification reactions are cyclic, by using the term "during the amplification reaction", it is meant that the LAC is added after the first amplification cycle, but before the last cycle.

After addition, the LAC is mixed into amplification reaction mixture. Such mixing can be done under a wide variety of conditions of time, temperature and types of mixing devices. Since these compounds are in aqueous solution, mixing by shaking after addition for more than 15 seconds should be adequate. If the sample solution is viscous, a longer period may be needed. Mixing time can easily be determined by one skilled in the art. Usually, such mixing can be carried out at ambient temperature, but an elevated temperature may also be used, so long as the integrety of the LAC is maintainable at this temperature.

To activate the LAC for covalent attachment with the target nucleic acids, the wavelength of choice is dependent on the photoactivatable moeties in LAC. For example, with furocoumarines like angelicin, wavelengths between 300 and 370 nm are preferred, and wavelengths between 320 and 350 nm are more preferred. For compounds like azideothidium, a longer wavelength light source may be desirable. Appropriate activation wavelengths can be found in the scientific literature for most photoactivatable intercalating compounds, or such wavelengths can be easily determined by one skilled in the art.

EXAMPLES

Example 1

Synthesis of Angelicine Bisbenzimidazole-PEG-biotin

In this example, synthesis of an LAC comprising a photoreactive ligand, a binding enhancer, a linker and a label is described. All four components are covalently linked to produce the final LAC complex.

Step 1: Synthesis of dihexadecyl-3-bromo-propanediol

In this step, the synthesis of a bifunctional linker is described, which is used to link together the photoreactive ligand and the binding enhancer. This same compound can easily be modified and used to link together other LAC components.

In a 210 mL round bottomed flask equipped with a magnetic stir bar, 2 g of dihexadecylglycerol (Sigma, St. Louis, Mo.) is dissolved into 120 mL of toluene. To this solution is added 3.54 g (10.7 mmoles) of carbon tetrabromide and 2.80 g (10.7 mmoles) of tripenylphosphine, and the reaction mixture is stirred overnight (18–20 hrs) at room temperature. The yellow suspension is filtered and the filtrate concentrated on a rotary evaporator to afford a white solid. This residue is dissolved into toluene, washed once with saturated sodium chloride, dried over anhydrous magnesium sulfate and concentrated under vacuum on a rotary evaporator to afford 2.5 g of crude product as a white powder. This crude product is purified by flask column chromatography on a silica gel 60 (E. Merck, Germany) column by sequential elution with 100 mL each of hexane, 14 ethyl acetate in hexane, 21 ethyl acetate in hexane and finally with 31 ethyl acetate in hexane. Fractions (8 mL) are collected and screened by thin-layer chromatography ("TLC") and those fractions that contain pure product (silica gel, 51 ethyl acetate in hexane) are pooled. The pooled fractions are concentrated under vacuum on a rotary evaporator to afford a quantitative yield of 1,2-0-dihexadecyl-3-bromo-1,2 propanediol as a white powder.

Step 2: Synthesis of Bisbenzimidazole Succinate Ester

In this step, synthesis of an active ester of a binding enhancer is described, which can then be easily conjugated to both the photoreactive ligand and the linker. A solution of bisbenzimidazole (6 g, 0.01 mol) dicyclohexylcarbodiimide (0.05 mol) and succinic acid (0.01 mol) in 100 mL of chloroform is stirred overnight (18–24 hrs). During this time, a white precipitate is formed. The precipitate is filtered of and washed with chloroform (2×50 mL). The combined chloroform is concentrated under vacuum in a rotary evaporator and the residue purified by flash column chromatography. The fractions containing the product is combined and concentrated under vacuum in a rotary evaporate to afford bisbenzimide succinnate ester (80%) as a white solid.

Step 3: Synthesis of pentaoxaheptadecane ditosylate

In this step, synthesis of a difunctional linker is described, which is used to link together the photoreactive ligand and the binding enhancer. To a stirred solution containing hexamethylene glycol (50 g, 0.18 mol) trimethylamine (40 g, 0.39 mol) in methylene chloride (400 mL) at 0° C. is added dropwise a solution of p-toluenesufonyl chloride (74 g, 0.39 mol). The reaction mixture is then stirred for ash at room temperature. The mixture is filtered and the filtrate concentrated under vacuum in a rotary evaporator. The residue is suspended in ethylacetate (500 mL) and filtered. The filtrate concentrated under vacuum to afford yellow oil. The yellow oil in triturated with hexane and the resulting oil vacuum dried to afford 108 g of yellow oil.

Step 4: Synthesis of Diphthalimido pentaoxaheptadecane ditosylate

A suspension of ditosylate (Step 3, 108 g), potassium phthalimide (75 g) in dimethylacetamide (700 mL) is heated at 165° C. for 2 hrs with vigorous stirring. The reaction mixture is then cooled to room temperature and the precipitate filtered off. The precipitate is washed with water and acetone to afford 53 g of the desired product as a white solid.

Step 5: Synthesis of Diamino pentaoxaheptadecane

A solution of diphthalimide (Step 4, 60 g), hydrazine hydrate (15 g) and ethanol (500 mL) is heated at 100° C. with stirring for 3 hours. The reaction mixture is cooled to room temperature and filtered. The solid is washed with cold ethanol. The combined filtrate is combined and concentrated under vacuum in a rotary evaporator to afford 33 g of yellow oil.

Step 6: Synthesis of 1-Amino-17-N-(Biotinylamido)-pentaoxaheptadecane

A solution of diaminopentaoxaheptadecane (Step 5, 7 g) in dimethyformamide is stirred at room temperature for 4 hours. This crude product was purified by flash column chromatography on silica gel 60 column. The fractions containing the product was pooled and concentrated under vacuum in a rotary evaporator to afford 2.5 g of waxy solid. The waxy solid was recrystalized from isopropanol/ether mixture to afford 1.8 g of white powder.

Step 7: Synthesis of bisbenzimidazole-PEG-bitotin

In this step, the binding enhancer is covalently linked to the difunctional linker and the label. A solution of biotinylamido pentaoxaheptadecane (Step 6, 3 g), bisbenzimidazole succinate ester (Step 2, 2 g) and dicydclohexylcarbodimide (5 g) in chloroform (200 mL) is stirred at room temperature for 20–24 hrs. The white precipitate formed is filtered off and the solid washed with chloroform. The combined chloroform is concentrated under vacuum in a rotary evaporator and the residue purified by flash column chromatography. The fractions containing the product is combined and concentrated under vacuum in a rotary evaporator to afford bisbenzamide-PEG-biotin as an off-white solid (1.5 g).

Step 8: Synthesis of Angelicine bisbenzimidazole-PEG-biotin

In this step, the final LAC complex is formed. To a solution of bisbenzimidazole-PEG-biotin (Step7, 0.4 mmol) in dimethylformamide is added N,N-carbonyldiimidazole (0.5 mmol). The resulting mixture is stirred for 3–5 hrs and is then treated with aminomethylangelicin (0.2 mmol), diispropylethylamine (150 ml) and dimethylformamide (100 ml). The reaction mixture is stirred overnight at 50–55° C. The mixture is evaporated under vacuum in a rotary evaporator and the residue is load onto a column of silica gel and eluted sequentially with 7% methanol in chloroform and 10% methanol in chloroform. The fractions containing the product were pooled and concentrated to afford (0.2 mmol) of the product as a glassy solid.

Example 2

Synthesis of Angelicine Bisbenzimidazole-PEG-acridine

The following example describes the synthesis of a LAC employing a chemiluminescent acridinium ester as the label.

Step 1: Synthesis of acrdinecarbonylchloride

A solution of acridine carboxyl acid (Aldrich) and thionyl chloride is stirred at room temperature for 20–24 h. Excess thionyl chloride is removed under vacuum in a rotary evaporator. The residue is treated with toluene and evaporated to remove traces of thionyl chloride.

Step 2: Synthesis of acridine-4-hydroxypropionic acid succinimide ester

A solution of acridine carbonyl chloride (2.3 g, Step 1) in dry pyridine (35 mL) is treated with hydroxyphenolpropionic acid N-hydroxysuccinimide ester (2.5 g) at room temperature for 8–24 h. The resulting triethylaminehydochloride is filtered off and the solution is concentrated under vacuum in a rotary evaporator to afford the succinimide ester as an off white solid.

Step 3: Synthesis of methyl fluorosulfonate succinimido acridine

A solution of succinimide ester (Step 2, 2 g) and methyl fluorosulfonate (3 mL) in dry chloroform is stirred for 8–24 h at room temperature. The resulting solid is filtered off and the solution concentrated under vacuum in a rotary evaporator to afford 1.5 g of product as a yellow solid.

Step 4: Synthesis of 1-amino-17-N(acridnylamido)-pentaoxaheptadecane

A solution of diaminopentaoxaheptadecane (Step 5, Example 1) in dimethyl formamide (75 mL) is treated with acridine NHS ester (Step 3). The resulting solution is stirred at room temperature for 4 hours. The solvent is removed under vacuum in a rotary evaporator and the residue is triturated with hexane to afford the compound as a pale yellow solid.

Step 5: Synthesis of bisbenzimidazole-PEG-acridine

A solution of acridinylamido pentaoxaheptadecane (Step 4), bisbenzimidazole succinic acid half ester (Step 2, Example 1 ) and dicyclohexylcarbodimide in chloroform is stirred at room temperature for 18–24 hours. The white precipitate is filtered off and the solid washed with chloroform. The combined chloroform is concentrated under vacuum in a rotary evaporation to afford the product as an off white solid.

Step 6: Synthesis of angelicine bisbenzimidazole-PEG-acridine

To a solution of bisbenzimidazole-PEG-acridine (Step 5) in dimethylformamide is added N,N-carbonyldiimidazole. The resulting mixture is stirred for 3–8 hours. And is then treated with aminomethyldimethylangelicine, diisopropylethylamine and dimethylformamide. The reaction mixture is stirred overnight at 50–55° C. The mixture is evaporated under vacuum in a rotary evaporator and the residue is purified by flash column chromatography on a column of silica gel. Sequential elution with 7% methanol in chloroform and 10% methanol in chloroform afforded fractions containing product. The fractions are pooled and concentrated to yield the desired product as a solid.

Example 3

Synthesis of Angelicine Bisbenzimidazole-PEG-azidonitrobenzene

The following example describes the synthesis of a LAC that has two intercalating moieties, one of which is used to couple the binding ligand to the nucleic acid, and the other of which is used to enhance binding of the LAC to the nucleic acid.

Step 1: Synthesis of bisbenzimidazole-PEG-azidonitrobenzene

A solution of diaminopentaoxaheptadecane (Step 5, Example 1) and sulfoSANPH (Pierce Chemicals) is stirred at room temperature overnight. The solution is concentrated under vacuum in a rotary evaporator and the residue is dissolved in dimethylformamide. The solution is then treated with bisbenzamide succinate ester (Step 2, Example 1) and stirred overnight. Following completion of reaction (TLC), the solution is concentrated to afford an off white crystaline solid.

Step 2: Synthesis of angelicine bisbenzimidazole-PEG-azidonitrobenzene

A solution of bisbenzimidazole-PEG-azidonitrobenzene (Step 1, Example 3) and N,N-carbonyldiimidazole in dimethylformamide is stirred for 4–14 hours at room temperature. The resulting mixture is treated with aminomethyldimethylangelicine, diisopropylethylamine and the resulting mixture is stirred overnight at 50–55° C. Following completion of reaction, the reaction mixture is concentrated in a rotary evaporator. The residue is purified by flash column chromatography on a column of silica gel. The column is eluted with a mixture of chloroform/methanol and the fractions containing product are pooled and concentrated to afford the product as a solid.

Example 4

Synthesis of Angelicine-DAPI-Biotin

In this example, the synthesis of another exemplary LAC is described using a different binding enhancer.

Step 1: Synthesis of 1-DAPI-17-pentaoxaheptadecane tosylate

A solution of pentaoxaheptadecane ditosylate (Step 3, Example 1), DAPI (Aldrich, Cat.No 21, 708-5) in dimethylsulfoxide is stirred at room temperature for 8–24 hours. Upon completion of the reaction (TLC), the reaction mixture is evaporated under vacuum in a rotary evaporator and the residue is loaded onto a column of silica gel and eluted with a solution of 0–50% methanol in chloroform. The fractions containing the product are pooled and the combined fractions concentrated under vacuum in a rotary evaporator to afford the product as an off white solid.

Step2: Synthesis of Angelicine-DAPI

A solution of 1-DAPI-17-pentaoxaheptadecane tosylate (Step 1, Example 4), aminomethyldimethylangelicine in dimthylformamide is stirred at 25–60° C. for 8–48 hours. Upon completion of the reaction (TLC), the reaction mixture is evaporated under vacuum in a rotary evaporator and the residue is loaded onto a column of silica gel and eluted with a solution of 0–30% methanol in chloroform containing trace of ammonia. The fractions containing the product are pooled and concentrated to afford the product as a pale yellow solid. The crude product is recrystallized from a mixture of dimethlformamide and hexane.

Step3: Synthesis of Angelicine-DAPI-Biotin

A solution of angelicine-DAPI (Step 2, Example 4), biotin-NHS ester (Sigma, Cat.No 1759 ) in dimthylformamide is stirred at 25–70° C. for 8–72 hours. Upon completion of the reaction, the reaction mixture is evaporated under vacuum in a rotary evaporated and the residue is treated with petroleum ether. The solid is collected by filtration and solid is washed with petroleum ether (3×50 ml). The crude solid is recrystallized to afford the product as a white solid.

Example 5

Demonstration of Inhibition of Amplification of a Nucleic Acid Amplicon by Photochemical Labeling with the Compounds Described in Example 1.

Nucleic acids are amplified following the protocols as describedby Whelan, et al, *Journal of Clinical Microbiology*, 33(3):556–561(1995) by PCR. In the PCR reaction mixture, two specific primers, dNTP, 0.25 U of Taq polymerase, and 1× PCR Buffer are used. For every 25 $\mu$l PCR reaction, 2 $\mu$l smaple (extracted chromosomal DNA from target organism) is added and amplified on a thermal cycler. The amplification cycle includes an initial denaturation, up to 50 cycles of annealing and strand separation (denaturation), and a final incubation for strand elongation.

In the amplification mixture before the initiation of amplification reaction photoreactive compounds are added such that their concentration in the final reaction mixture is between 0.1 and 1,000 nanomolar. After the amplification is completed the reaction mixture is exposed to 330±30 nm light by using a commercially available transilluminator (TL-33, UV Products, San Gabriel, Calif., USA) for one hour. After the photoreaction the amplicons are detected by gel electrophoresis. 5 $\mu$l in 2.5% (wt/vol) agarose in TBE buffer (0.089 M Tris-0.089 M borate-2 mM EDTA), followed by staining with ethidium bromide.

A part of the amplicon mixture (2 $\mu$l) is then further amplified by adding fresh solutions of same primers, enzymes and other reagents. The negative results of the second amplification reaction indicate that the photoreaction has substantially protected the amplicons from polymerase mediated amplification reactions.

Example 6

Detection of Amplicons by Photolabeling

Unlabelled 0.5 $\mu$g DNA probes complementary to the amplicons of example 1 are immobilized by spotting onto nitrocellulose paper as described by Dattagupta et al,.*Perspectives in Antiinfective Therapy*, Jackson et al., Ed., Friedr. Vieweg & Sohn Verlagsgesellschaft mbH, Braunschweig 1989, pages 241–247. Amplicons from amplification reactions are photolabelled as described in example 1 or by adding biotin-PEG-angelicin instead of the compound of example 1 to the amplification reaction mixture and irradiating the mixture to 340±30 nm light for one hour.

These photolabelled amplicons are allowed to hybridize to immobilized DNA probes on nitrocellulose paper. Hybridized nucleic acids can be detected with chemiluminescence by adding anti-biotin-linked horseradish peroxidase and assaying for peroxidase with $H_2O_2$ and isoluminol. Emitted light form a positive reaction is detected with Polaroid films.

Example 7

Labeling and Sterilization with Compounds with Enhanced Nucleic Acid Binding Properties.

Experiments similar to Examples 5 and 6 are carried out with compounds comprising furocoumarines that are covalently linked to a binding enhancer as described in Examples 1–4. These compounds show enhanced binding and sterilization properties for amplicons.

Example 8

Sterilization of TMA Amplicons Using Compounds of Examples 1–4.

Nucleic acids are amplified following the protocols as described by Wylie et al., *Journal of Clinical Microbiology*, 36(12):3488–3491 (1998) by TMA. In the TMA reaction, nucleic acid targets are captured with magnetic beads and specific captured primers. Then, captured targets are washed and pelleted before adding amplification reagents which contains amplification primers, dNTP, NTP, 2500 U of reverse transcriptase and 2500 U of T7 RNA polymerase. For a 100 $\mu$l TMA reaction, 200 $\mu$l oil reagent is added and amplified at 42° C. on a waterbath for an hour.

In the amplification mixture before the initiation of the amplification reaction, the photoreactive compounds described in Examples 1–4 are added such that their concentration in the final reaction mixture is between nanomolar and millimolar (100 $\mu$g/ml). After the amplification is completed, the reaction mixture is exposed to 340±30 nm light for one hour. After the photoreaction, 100 $\mu$l AE-labeled probe is added to the amplicon for detection purpose. Unhybridized AE-probe is destroyed by 300 $\mu$l Selection Reagent through the HPA reaction. Hybridized amplicon and AE-probe then is detected with a Gen-Probe (San Diego, Calif.) Leader 450 luminometer.

A part of the amplicon mixture (5 $\mu$l) is further amplified by adding to a negative amplification tube which contains fresh solutions of same primers, enzymes and other reagents except targets. The negative results of the second amplification reaction indicate that the photoreaction has substantially protected the amplicons from TMA amplification reactions.

Example 9

Sterilization of LCR Amplicons Using Compounds of Examples 1–4.

Nucleic acids are amplified following the protocols as described by Moore et al., *Journal of Clinical Microbiology* 36(4):1028–1031 (1998) by LCR. In the LCR reaction mixture, two pair of probes, dNTP, DNA ligase and DNA polymerase are used. To a LCx tube containing 90 μl LCR reagents, 100 μl sample (extracted chromosomal DNA from target organism) is added and amplified on a LCx thermal cycler.

In the amplification mixture before the initiation of amplification reaction photoreactive compounds are added such that their concentration in the final reaction mixture is between 0.01 nanomolar and 10.0 millimolar. After the amplification is completed, the reaction mixture is exposed to 340±30 nm light for one hour. After the photoreaction, the amplicons are detected by gel electrophoresis of 5 μl in 2.5% (wt/vol) agarose in TBE buffer (0.089 M Tris-0.089 M borate-2 mM EDTA), followed by staining with ethidium bromide.

A part of the amplicon mixture (2 μl) is then further amplified by adding fresh solutions of same primers, enzymes and other reagents. The negative results of the second amplification reaction indicate that the photoreaction has substantially protected the amplicons from polymerase mediated amplification reactions.

Example 10

Sterilization of SDA Amplicons Using Compounds of Example 1–4

Nucleic acids are amplified following the protocols as described by Walker, et al., *Nucleic Acids Res.*, 20(7):1691–1696 (1992) by SDA. The SDA reaction mixture contains four SDA primers, dGTP, dCTP, TTP, dATPS, 150 U of Hinc II, 5 U of exonuclease deficient *E. coli* DNA polymerase I. The sample mixture is heated 95° C. for 4 minutes to denature target DNA prior to addition of the enzymes. After addition of the two enzymes, the amplification is carried out for 120 min at 37° C. in a total volume of 50 μl. Then, the reaction is terminated by heating 2 minutes at 95° C.

In the amplification mixture before the initiation of amplification reaction photoreactive compounds are added such that their concentration in the final reaction mixture is between nanomolar and millimolar (100 μg/ml). After the amplification is completed the reaction mixture is exposed to 340±30 nm light for one hour. After the photoreaction the amplicons are detected by gel electrophoresis of 5 μl in 2.5% (wt/vol) agarose in TBE buffer, followed by staining with ethidium bromide, like in example 1.

A part of the amplicon mixture (5 μl) is then further amplified by adding to a negative amplification tube which contains fresh solutions of same primers, enzymes and other reagents except targets. The negative results of the second amplification reaction indicate that the photoreaction has substantially protected the amplicons from SDA amplification reactions.

Example 11

Sterilization of NASBA Amplicons

Nucleic acids are amplified following the protocols as described in Heim, et al., *Nucleic Acids Res.*, 26(9):2250–2251 (1998) by NASBA. The NASBA reaction mixture contains two specific primers, dNTP, NTP, 6.4 U of AMV reverse transcriptase, 0.08 U of Escherichia coli Rnase H, and 32 U of T7 RNA polymerase. The amplification is carried out for 120 min at 41° C. in a total volume of 20 μl.

In the amplification mixture before the initiation of amplification reaction photoreactive compounds are added such that their concentration in the final reaction mixture is between nanomolar and millimolar (100 μg/ml). After the amplification is completed the reaction mixture is exposed to 340±30 nm light for one hour. After the photoreaction the amplicons are detected by gel electrophoresis of 5 μl in 2.5% (wt/vol) agarose in TBE buffer, followed by staining with ethidium bromide like in example 5.

A part of the amplicon mixture (5 μl) is then further amplified by adding to a negative amplification tube which contains fresh solutions of same primers, enzymes and other reagents except targets. The negative results of the second amplification reaction indicate that the photoreaction has substantially protected the amplicons from NASBA amplification reactions.

Example 12

Labeling of Nucleic Acids with Compounds of Example 1–4.

Clinical urine samples suspected of urinary tract infection are used. To 1 ml urine sample in a polypropylene microfuge tube, 0.1 ml 1N sodium hydroxide is added and heated for 15 minutes at 90° C. To this solution, 0.1 ml 1N hydrochloric acid is added for neutralization. To the lysed solution, compounds of Examples 1–4 dissolved in water is added so that the final concentration is 1.0 micromolar. The mixture is then exposed to light of wavelengths between 330±30 nm. The labeled samples are detected by hybridization with immobilized probe panels as described in U.S. Pat. No. 5,348,855.

A similar experiment is done with nucleic acids extracted from the urine samples by precipitating lysed nucleic acids from urine followed by phenol and chloroform extraction as described by J. Marmour, *Journal of Mol. Biol.*, 3:208–218 (1961).

Example 13

Microarray Hybridization and Detection of Amplicons After Photochemical Labeling with the Compound of Example 1

Troesch et al., *Journal of Clinical Microbiology*, 37(1):49–55 (1999) describe an assay using an array of probes immobilized onto a microchip. The PCR amplification reaction is done as described in the reference. After PCR instead of transcription to produce RNA, the amplicon DNA is labeled with the compound of Example 1 as described in Example 5. The labeled amplicon is hybridized for 16 hours and detected using fluorescently labeled streptavidin using the devices described therein.

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A complex for labeling a nucleic acid in a sample comprising:
   a photoreactive binding ligand comprising a chemical moiety that binds to a nucleic acid and that, when activated by light, forms at least one covalent bond therewith;
   a binding enhancer comprising a chemical moiety that has a specific affinity for nucleic acids; and
   a label comprising a detectable chemical moiety;
   wherein said binding ligand, binding enhancer and label are bound together in the form of a covalent or noncovalent complex.

2. The composition of claim 1, wherein the binding ligand is an intercalator compound.

3. The composition of claim 2, wherein the intercalator compound is a furocoumarin or a phenanthridine.

4. The composition of claim 2, wherein the intercalator compound is monoadduct forming.

5. The composition of claim 4, wherein the intercalator compound is an angelicin derivative.

6. The composition of claim 2, wherein the binding ligand is a non-intercalating compound.

7. The composition of claim 6, wherein the non-intercalating compound is selected from the group comprising benzimides, netropsins and distamycins.

8. The composition of claim 1, wherein the binding enhancer is an intercalator compound.

9. The composition of claim 8, wherein the binding enhancer is monoadduct forming.

10. The composition of claim 1 wherein the binding enhancer is a non-intercalating compound.

11. The composition of claim 10, wherein the non-intercalating compound is selected from the group consisting of an oligo pyrrole, a phenyl indole, a nucleic acid and a protein.

12. The composition of claim 1, wherein the binding enhancer has an affinity for nucleic acids equal to or greater than $1 \times 10^4$ mole$^{-1}$.

13. The composition of claim 1, wherein the binding enhancer specifically binds to nucleic acids in the presence of greater than 10 mM magnesium.

14. The composition of claim 1, wherein the label is a fluorophore.

15. The composition of claim 1, wherein the label is chemiluminescent.

16. The composition of claim 1, wherein the label is a chromophore.

17. A composition for labeling and decontaminating a nucleic acid amplification reaction product comprising at least two intercalator moieties and a detectable label, wherein at least one of said intercalator moieties forms at least one covalent bond with said nucleic acid amplification reaction product.

18. A method for labeling and decontaminating nucleic acids in an amplification reaction mixture comprising the steps of:
   preparing a nucleic acid amplification reaction mixture;
   contacting the mixture with a composition according to claim 1; and
   exposing the mixture to light of an appropriate length of time and wavelength to cause the binding ligand to become covalently attached to nucleic acids in the amplification reaction mixture.

19. The method of claim 18, wherein the binding ligand is an intercalating compound.

20. The method of claim 19, wherein both the binding ligand and the binding enhancer are intercalating compounds.

21. A method of preventing a nucleic acid from serving as a template in an amplification reaction, comprising the steps of:
   contacting a nucleic acid with a composition according to claim 1 to form a mixture; and
   exposing the mixture to light of an appropriate length of time and wavelength to cause the binding ligand to become covalently attaches to the nucleic acid in the mixture.

22. The method of claim 18, wherein said step of contacting the mixture with the composition according to claim 1 is performed before amplification.

23. The method of claim 18, wherein said step of contacting the mixture with the composition according to claim 1 is performed during amplification.

24. The method of claim 18, wherein said step of contacting the mixture with the composition according to claim 1 is performed after amplification.

25. A complex for labeling a nucleic acid in a sample comprising:
   a photoreactive binding ligand comprising a chemical moiety that binds to a nucleic acid and that, when activated by light, forms at least one covalent bond therewith;
   a binding enhancer comprising a chemical moiety that has a specific affinity for nucleic acids; and
   a label comprising a detectable moiety; and
   at least one lysis reagent;
   wherein said binding ligand, binding enhancer and label are bound together in the form of a covalent or noncovalent complex.

26. The composition of claim 25, wherein the binding ligand is an intercalator compound.

27. The composition of claim 26, wherein the intercalator compound is a furocoumarin or a phenanthridine.

28. The composition of claim 26, wherein the intercalator compound is monoadduct forming.

29. The composition of claim 28, wherein the intercalator compound is an angelicin derivative.

30. The composition of claim 26, wherein the binding ligand is a non-intercalating compound.

31. The composition of claim 30, wherein the non-intercalating compound is selected from the group consisting of benzimides, netropsins and distamycins.

32. The composition of claim 25, wherein the binding enhancer is an intercalator compound.

33. The composition of claim 32, wherein the binding enhancer is monoadduct forming.

34. The composition of claim 25, wherein the binding enhancer is a non-intercalating compound.

35. The composition of claim 34, wherein the non-intercalating compound is selected from the group consisting of an oligo pyrrole, a phenyl indole, a nucleic acid and a protein.

36. The composition of claim 25, wherein the binding enhancer has an affinity for nucleic acids equal to or greater than $1 \times 10^4$ moles$^{-1}$.

37. The composition of claim 25, wherein the binding enhancer specifically binds to nucleic acids in the presence of greater than 10 mM magnesium.

38. The composition of claim 25, wherein the label is a fluorophore.

39. The composition of claim 25, wherein the label is chemiluminescent.

40. The composition of claim 25, wherein the label is a chromophore.

41. A method for labeling a nucleic acid in a clinical sample, comprising the steps of:
  adding a photoreactive binding ligand to the clinical sample, wherein the binding ligand comprises a chemical moiety that binds to a nucleic acid and, when activated by light, forms at least one covalent bond therewith;
  adding a binding enhancer to the clinical sample, wherein the binding enhancer comprises a chemical moiety that has a specific affinity for nucleic acids; and
  adding a label comprising a detectable moiety; and
  at least one lysis reagent;
  wherein said binding ligand, binding enhancer and label are bound together in the form of a covalent or noncovalent complex.

42. The method of claim 41, wherein the binding ligand is an intercalating compound.

43. The method of claim 42, wherein both the binding ligand and the binding enhancer are intercalating compounds.

44. The method of claim 41, wherein the binding ligand, binding enhancer, and label are chemically linked as a conjugate.

45. The method of claim 41, wherein the binding ligand, binding enhancer, label and lysis reagent(s) are added together to the clinical sample.

* * * * *

UNITED STATES PATENT AND TRADEMARK OFFICE
CERTIFICATE OF CORRECTION

PATENT NO.      : 6,187,566 B1
DATED           : February 13, 2001
INVENTOR(S)     : Dattagupta et al.

It is certified that error appears in the above-identified patent and that said Letters Patent is hereby corrected as shown below:

<u>Column 9,</u>
Lines 3-10, please delete the paragraph and substitute therefor:

A solution of diaminopentaoxaheptadecane (Step 5, 7 g) <u>and N-succinimidyl biotin (3.41g)</u> in dimethyformamide is stirred at room temperature for 4 hours. This crude product was purified by flash column chromatography on silica gel 60 column. The fractions containing the product was pooled and concentrated under vacuum in a rotary evaporator to afford 2.5 g of waxy solid. The waxy solid was recrystalized from isopropanol/ether mixture to afford 1.8 g of white powder.

Signed and Sealed this

Fifteenth Day of July, 2003

JAMES E. ROGAN
*Director of the United States Patent and Trademark Office*